United States Patent [19]

Piotrowski et al.

[11] Patent Number: 4,885,406

[45] Date of Patent: Dec. 5, 1989

[54] HYDROCARBON-SOLUBLE COMPLEXES OF MAGNESIUM ALKOXIDES WITH MAGNESIUM ARYL OXIDES

[75] Inventors: Andrzej M. Piotrowski, Thornwood, N.Y.; Dennis B. Malpass, LaPorte, Tex.

[73] Assignee: Texas Alkyls, Inc., Deer Park, Tex.

[21] Appl. No.: 215,121

[22] Filed: Jul. 5, 1988

[51] Int. Cl.$^4$ ............................................. C07C 39/00
[52] U.S. Cl. .................................... 568/716; 568/851
[58] Field of Search ...................... 568/715, 851, 716

[56] References Cited

U.S. PATENT DOCUMENTS

| | | | |
|---|---|---|---|
| 3,657,361 | 4/1972 | Lenz et al. | 568/851 |
| 3,920,713 | 11/1975 | Feichtinger | 568/851 |
| 4,178,300 | 12/1979 | van den Berg | 568/851 |
| 4,518,807 | 5/1985 | Hori et al. | 568/716 |
| 4,634,786 | 1/1987 | Kamienski | 568/851 |
| 4,683,344 | 7/1987 | Hodek et al. | 568/716 |
| 4,691,057 | 9/1987 | Eisenbraun | 568/716 |

*Primary Examiner*—Werren B. Lone
*Attorney, Agent, or Firm*—Richard P. Fennelly; Louis A. Morris

[57] ABSTRACT

Hydrocarbon-soluble complexes of magnesium alkoxides with magnesium aryl oxides are described. The magnesium aryl oxide moiety is derived from a hindered aromatic alcohol. The complexes can be formed by reaction between a magnesium alkyl and a mixture of aliphatic alcohols and a hindered aromatic alcohol.

4 Claims, No Drawings

HYDROCARBON-SOLUBLE COMPLEXES OF MAGNESIUM ALKOXIDES WITH MAGNESIUM ARYL OXIDES

BACKGROUND OF THE INVENTION

1. Field of the Invention

The current invention relates to hydrocarbon-soluble complexes of magnesium alkoxides with magnesium aryl oxides.

2. Description of the Prior Art

Recent interest has focused upon deriving hydrocarbon-soluble magnesium alkoxides which can function, for example, as catalyst precursors.

U.S. Pat. No. 4,178,300 to van den Berg mentions that solutions of organooxy magnesium compounds of desirably low viscosity can be prepared by dissolving a magnesium compound of that type in the presence of an organooxy compound of a transition metal from Groups IV through VI of the Periodic Table. Representative transition metal compounds include those of titanium, zirconium, vanadium, and chromium. Preferred transition metal compounds are those of titanium.

More recently, U.S. Pat. No. 4,634,786 of C. W. Kamienski indicates that magnesium primary dialkoxides having 2-alkyl substituents in the alcohol moiety possess good solubility, especially in the presence of minor amounts of aluminum alkoxides and lithium or potassium alkoxides derived from the same alcohol moiety.

SUMMARY OF THE PRESENT INVENTION

It has now been found that it is possible to solubilize magnesium alkoxides by forming hydrocarbon-soluble complexes of magnesium alkoxides with magnesium aryl oxides. For example, such complexes can be formed by utilizing ligands on a magnesium atom derived from aliphatic alcohols (or mixtures thereof) in conjunction with a highly hindered aromatic alcohol.

DETAILED DESCRIPTION OF THE PRESENT INVENTION

The hydrocarbon-soluble complexes of magnesium alkoxides with magnesium aryl oxides that are contemplated by the present invention are easily formed by conducting a reaction between a magnesium alkyl and the desired mixture of aliphatic alcohols and hindered aromatic alcohol in an appropriate solvent. The hydrocarbon soluble complexes of magnesium alkoxides with magnesium aryl oxides that are contemplated by the present invention can be easily formed by conducting a reaction between a magnesium alkyl and the desired mixture of aliphatic alcohols and hindered phenol in an appropriate solvent. Since heating of the mixture of such components facilitates the desired reaction, solvents which boil above about 90° C. (e.g., heptane or toluene) are most suitable. Such a reaction insures that the resulting composition is a complex of magnesium alkoxides and magnesium aryl oxides having the formula $Mg(OR)_x(OR')_y$ where R is either straight or branched alkyl such as n-butyl, 2-ethyl-1-hexyl, n-decyl, and so forth. The moiety R' is derived from a highly hindered aromatic alcohol or phenol. This phenol can have the formula

where Ar is a phenyl ring and $R^1$ and $R^2$ are branched alkyl groups such as butyl (tert- or sec-), isopropyl, neopentyl and the like, and $R^3$ is linear or branched hydrocarbyl, e.g., alkyl or is phenyl, or is hydrogen. A representative example of such phenol is 2,6-di-t-butyl-4-methylphenol, also known as "butylated hydroxy toluene". Others include 2,6-di-neopentyl-4-methylphenol, 2,6-di-isopropyl-4-ethylphenol, and 2,6-di-sec-butyl-4-methylphenol. Generally speaking, the values for x and y individually can range anywhere from about 0.1 to about 1.9 with the sum of x and y being substantially equal to 2.

The foregoing invention is further illustrated by the Examples which follow.

COMPARATIVE EXAMPLE A

To 320 grams of a 15% solution of n-butylethyl-magnesium (BEM) (38.1 grams or 0.526 mole) in heptane cooled in an oil bath, a mixture of n-butanol (37 grams of 0.50 mole) and 2-ethyl-1-hexanol (32.5 grams of 0.25 mole) was added slowly. Temperature of the oil bath and rate of addition were adjusted to warm the reaction mixture to 65° C. at the end of the addition. Some solids were formed during the reaction but were redissolved upon stirring for about 15 minutes at 65° C. The solution formed was clear and colorless but somewhat viscous. It was cooled and stored overnight at ambient temperature. Viscosity of the solution increased overnight such that the material was no longer transferable.

COMPARATIVE EXAMPLE B

To 64.1 grams of a 22% solution of BEM (0.128 mole) in heptane, a mixture of 6.9 grams of n-butanol (0.093 mole) and 21.8 grams of 2-ethyl-1-hexanol (0.167 mole) was added. After the addition was completed, the pot was heated to reflux (approximately 95° C.) for one hour. A clear, colorless, very viscous (even at 95° C.) solution was formed which turned into a glass at room temperature.

EXAMPLE 1

To 55.3 grams of a 22% solution of BEM (0.112 mole) in heptane, a mixture of 26.51 grams of n-decanol (0.167 mole), 2.06 grams n-butanol (0.028 mole) and 6.15 grams of butylated hydroxy toluene (BHT) (0.028 mole) was added slowly. After approximately half of the mixture of alcohols was added, the reaction mixture was heated to 75° C. The temperature was then slowly raised (by external heating) to reach 100° C. at the end of addition (one hour). A small amount of solids formed during the course of the reaction, but were redissolved upon stirring at reflux (approximately 100° C.) for one hour. A pale yellow non-viscous solution was formed.

EXAMPLE 2

To 248 grams of a 16% solution of BEM (0.36 mole) in heptane, there was slowly added 30 ml of n-BuOH (0.33 mole) over a period of 20 minutes. After an additional ten minutes of stirring at 65° C., 47 grams of BHT (0.21 mole) was added over a period in several portions over a period of 25 minutes. The reaction mixture was then refluxed for one half hour and 0.4 ml triethylaluminum (TEAL) was added to adjust the Mg/Al ratio to 45 (analyzed ratio was 80 before TEAL addition and 50 after addition). A free-flowing clear, colorless solution was obtained.

EXAMPLE 3

To 118.0 grams of a 22% solution of BEM (0.235 mole) in heptane there was slowly added a mixture of 16.2 grams of n-butanol (0.219 mole) and 19.0 grams of 2-ethyl-1-hexanol (0.146 mole). At the end of the addition, the reaction mixture was heated to reflux (approximately 95° C.) for one hour. The pot was then cooled and 26.8 grams of BHT (0.122 mole) were added as a solid over a period of 15 minutes. The reaction mixture was warmed to reflux for one hour. A yellow mobile solution was obtained.

EXAMPLE 4

Preparation was conducted as described in Example 3 using BEM (0.237 mole), 14.3 grams of n-butanol (0.193 mole), 25.2 grams of 2-ethyl-1-hexanol (0.194 mole) and 21.5 grams of BHT (0.098 mole). A yellow mobile solution was obtained.

EXAMPLE 5

Preparation was conducted as described in Example 3 using BEM (0.225 mole), 8.6 grams of n-butanol (0.116 mole), 36.2 grams of 2-ethyl-1-hexanol (0.278 mole) and 15.3 grams of BHT (0.070 mole). A yellow mobile solution was obtained.

ANALYSIS AND PHYSICAL PROPERTIES OF PRODUCTS

| Example | Mg Wt. % | Viscosity (Centipoise at 25° C.) | Density (g/ml at 25° C.) |
|---|---|---|---|
| A | 3.00 | >>1000 | — |
| B | — | glass | — |
| 1 | 3.56 | 46 | 0.798 |
| 2 | 3.76 | 8.6 | 0.746 |
| 3 | 3.73 | 41 | 0.804 |
| 4 | 4.18 | 19 | 0.827 |
| 5 | 3.65 | 35 | 0.804 |

The foregoing Examples represent certain preferred embodiments of the present invention and should not, therefore, be construed in a limting sense. The scope of protection that is sought is set forth in the claims which follow.

We claim:

1. A hydrocarbon-soluble complex of a magnesium alkoxide and a magnesium aryl oxide of the formula $Mg(OR)_x(OR')_y$, where R is alkyl and R' is derived from a hindered phenol, and x and y can range from about 0.1 to about 1.9 with their sum being substantially equal to 2.

2. A complex was claimed in claim 1 wherein the hindered phenol is 2,6-di-t-butyl-4-methylphenol.

3. A complex as claimed in claim 1 wherein the hindered phenol is of the formula $R^1Ar(OH)(R^2)(R^3)$, where Ar is phenyl and $R^1$ and $R^2$ are branched alkyl and $R^3$ is linear or branched hydrocarbyl or is hydrogen.

4. A complex as claimed in claim 1 wherein the phenol is 2,6-di-t-butyl-4-methylphenol and R is selected from the group consisting of butyl, 2-ethylhexyl, and decyl.

* * * * *